United States Patent
Hagiya

(10) Patent No.: US 7,132,092 B2
(45) Date of Patent: Nov. 7, 2006

(54) METALLIZED MESOPOROUS SILICATE AND METHOD OF OXIDATION WITH THE SAME

(75) Inventor: Koji Hagiya, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 124 days.

(21) Appl. No.: 10/503,499

(22) PCT Filed: Feb. 5, 2003

(86) PCT No.: PCT/JP03/01154

§ 371 (c)(1),
(2), (4) Date: Aug. 5, 2004

(87) PCT Pub. No.: WO03/066524

PCT Pub. Date: Aug. 14, 2003

(65) Prior Publication Data

US 2005/0090688 A1   Apr. 28, 2005

(30) Foreign Application Priority Data

Feb. 8, 2002   (JP) ............... 2002-032559

(51) Int. Cl.
- C01B 33/20 (2006.01)
- C07C 51/16 (2006.01)
- B01J 23/00 (2006.01)

(52) U.S. Cl. .................. 423/326; 423/423; 423/593.1; 423/594.8; 423/594.13; 502/247; 502/254; 502/255; 562/544; 562/547

(58) Field of Classification Search ............... 423/326, 423/702, 593.1, 594.8, 594.13; 502/247, 502/254, 255; 562/544, 547
See application file for complete search history.

(56) References Cited

U.S. PATENT DOCUMENTS

| | | | |
|---|---|---|---|
| 5,712,402 A * | 1/1998 | Pinnavaia et al. ......... 552/309 |
| 6,239,315 B1 | 5/2001 | Muller et al. | |
| 2001/0011148 A1 | 8/2001 | Mueller et al. | |
| 2001/0018399 A1 | 8/2001 | Rocca et al. | |
| 2002/0072637 A1 | 6/2002 | Klaas et al. | |
| 2003/0188991 A1* | 10/2003 | Shan et al. .............. 208/113 |
| 2004/0144726 A1* | 7/2004 | Chmelka et al. .......... 210/660 |

FOREIGN PATENT DOCUMENTS

| | | | |
|---|---|---|---|
| DE | 19910145 A1 * | 8/2000 |
| GB | 2252556 A | 8/1992 |
| JP | 4-49261 A | 2/1992 |
| JP | 2001-232205 A | 8/2001 |
| JP | 2001-523235 A | 11/2001 |
| JP | 2002-508746 A | 3/2002 |
| WO | WO00/07710 A1 * | 2/2000 |

OTHER PUBLICATIONS

Corma et al., Chem. Commun., pp. 2190-2191, (2001).
Briot et al., J. Mater. Chem., vol. 10, pp. 953-958, (2000).
Chavan et al., Synlett, No. 2, pp. 267-268, (2002).
Derouane et al., New J. Chem., pp. 797-799, (1998).
Gopinath et al., Organic Letters, vol. 2, No. 5, pp. 577-579, (2000).
Corma et al., Nature, vol. 412, p. 423-425, (2001).
Piquemal et al., Chem. Commun., pp. 1195-1196, (1999).
Piquemal et al., Micro. & Meso. Matls., vol. 29, pp. 291-304, (1999).
Corma et al., J. of Catalysis, vol. 145, pp. 151-158, (1994).
Jin et al., Chemistry Letters, pp. 371-372, (1999).
Reddy et al., J. Chem. Soc. Chem. Commun., pp. 1059-1060, (1994).
Sudhakar et al., J. Chem. Soc. Chem. Commun., pp. 2231-2232, (1995).
Zhang et al., Chem. Commun., pp. 979-980, (1996).
Zhang et al., Chem. Commun., pp. 241-242, (1998).
Zhang et al., Applied Catalysis A: General, vol. 179, pp. 11-19, (1999).

* cited by examiner

*Primary Examiner*—David Sample
(74) *Attorney, Agent, or Firm*—Birch, Stewart, Kolasch & Birch, LLP

(57) ABSTRACT

A metallized mesoporous silicate which is obtained by (i) reacting (a) either a metal peroxide obtained by the reaction of an aqueous hydrogen peroxide solution with at least one metal or metal compound selected from the group consisting of the following 1) to 4) 1) tungsten 2) molybdenum 3) vanadium 4) compounds comprising 4a) any of tungsten, molybdenum, and vanadium and 4b) at least one element selected from Groups 13 to 16 (excluding oxygen) or a solution of the metal peroxide with (b) a silicon compound in the presence of an alkylamine or a quaternary ammonium salt and separating the resultant silicate; and a process for producing the metallized mesoporous silicate. Also provided is a method of organic synthesis with the silicate.

13 Claims, 1 Drawing Sheet

METALLIZED MESOPOROUS SILICATE AND METHOD OF OXIDATION WITH THE SAME

TECHNICAL FIELD

The present invention provides a novel metallized mesoporous silicate comprising at least one member selected from tungsten, molybdenum and vanadium, a process for producing the same, and a method of oxidizing an organic compound using the metallized mesoporous silicate as a catalyst.

BACKGROUND ART

Hydrogen peroxide is a clean and excellent oxidizing agent which is inexpensive, and easily handled, and becomes harmless water after reaction, and an oxidation reaction using hydrogen peroxide as an oxidizing agent has been highlighted as one of environmentally friendly production processes. In development of an oxidation reaction using hydrogen peroxide as an oxidizing agent, it is important to develop a catalyst for the oxidation reaction. In particular, from the industrial viewpoint, it has been desired to develop a solid catalyst which is advantageous to separation and recovery of a catalyst from a reaction system. For example, regarding a titanium-containing mesoporous silicate which is one of solid catalysts, industrial utilization as an epoxidation catalyst of olefin compounds and as a catalyst for ammoximation of ketone compounds has been studied.

On the other hand, a solid catalyst containing a metal other than titanium and having different catalytic performance and catalytic activity from a titanium-containing mesoporous silicate has also been developed. For example, regarding a tungsten-containing mesoporous silicate, as a catalyst for producing cyclohexanediol by reacting cyclohexene and hydrogen peroxide, Applied Catalysis A, 179, 11 (1999), and Chem. Commun., 241 (1998) report a tungsten-containing mesoporous silicate produced by reacting a tetraalkoxysilane and ammonium tungstate using cetyl pyridinium bromide as a template in a strongly acidic solvent. However, such a tungsten-containing mesoporous silicate alone has low activity and, in order to obtain sufficient activity, acetic acid should be used as a reaction solvent.

For example, regarding a molybdenum-containing mesoporous silicate, as a catalyst for producing phenol by reacting benzene and hydrogen peroxide, Chem. Commun., 979 (1996) reports a molybdenum-containing mesoporous silicate produced by reacting potassium molybdate and a tetraalkoxysilane in a water-ethanol solvent in the presence of dodecylamine, filtering and washing the reaction product, and calcining the resulting crystals at 923K.

For example, regarding a vanadium-containing mesoporous silicate, as a catalyst for producing a quinone compound by reacting phenol or naphthol and hydrogen peroxide, J. Chem. Soc., Chem. Commun., 2231 (1995), p. 2231, left column, middle paragraph, and J. Chem. Soc., Chem. Commun., 1059 (1994) report a vanadium-containing mesoporous silicate obtained by reacting a solution obtained by adding vanadium sulfate to tetraalkoxysilane in a mixed solution of ethanol and isopropanol, with an aqueous solution containing dodecylamine and hydrochloric acid, filtering and washing the resulting crystals, and calcining them. In addition, from the results of XRD spectrum measurement, these silicate compounds are reported to be all MCM-41 type.

Further, regarding an oxidation reaction using hydrogen peroxide as an oxidizing agent, an oxidation reaction for an olefin compound and a Baeyer-Villiger oxidation reaction for a ketone compound are important, and a method using a solid catalyst has also been proposed. For example, a 2-alkoxyalcohol compound is generally produced by a two-stage method, wherein an olefin compound is once oxidized to convert it into an epoxide compound and then the epoxide compound is reacted with an alcohol compound. U.S. Pat. No. 6,239,315 proposes a one-stage process for producing a 2-alkoxyalcohol compound by reacting an olefin compound, hydrogen peroxide and an alcohol compound using two kinds of solid catalysts having different performances of a titania silicate catalyst having oxidation catalytic capability and a ZSM-5 catalyst having alkylation catalytic capability. However, there was a problem that two kinds of the expensive compounds should be used as the catalysts. As a method without using such two kinds of compounds as catalysts, New. J. Chem., 1998, 797–799 reports a method using a titanium-containing β-type zeolite. However, since a diol is produced as a by-product, selectivity of a 2-alkoxyalcohol is not high and, in order to prevent production of a diol as a by-product, anhydrous hydrogen peroxide should be used, which is problematic from the viewpoint of prevention of disasters.

Furthermore, as a method for obtaining a lactone compound or an ester compound by subjecting a ketone compound to a Baeyer-Villiger oxidation with hydrogen peroxide, for example, Nature, 412, 423 (2001), and Chem. Commun., 2190 (2001) report a method using a zeolite-β catalyst carrying tin, and JP 2001-232205 A reports a method using a silica catalyst carrying antimony fluoride. However, these methods use toxic tin and expensive antimony fluoride, and they can not be necessarily said to be industrial catalysts.

Moreover, as a method for obtaining an aromatic ester compound by using an aromatic aldehyde compound, hydrogen peroxide and an alcohol solvent, for example, a method using TS-1 as a catalyst (SynLett, 267 (2002)) and a method of using vanadium oxide and perchloric acid together (Organic Lett., 2, 577 (2000)) are reported. However, in the former, the reaction yield is low and, in the latter, perchloric acid which requires careful handling should be used together. Therefore, these catalysts can not necessarily be said to be industrial catalysts.

DISCLOSURE OF INVENTION

Under these circumstances, in order to develop a novel solid catalyst exhibiting catalytic activity in an oxidation reaction, the present inventor has studied intensively, and have found that a metallized mesoporous silicate containing at least one member selected from tungsten, molybdenum and vanadium which is obtained by reacting a silicon compound with a metal oxide obtained by reacting at least one member selected from tungsten metal, molybdenum metal, vanadium metal, the following tungsten compound, the following molybdenum compound and the following vanadium compound, which are easily available, with an aqueous hydrogen peroxide solution, in the presence of an alkylamine or a quaternary ammonium salt, exhibits good oxidizing catalytic activity in a reaction between an organic compound and hydrogen peroxide, and further exhibits not only oxidizing catalytic activity, but also catalytic activity in an alkylation reaction. Thus, the present invention has been accomplished.

That is, the present invention provides:

a metallized mesoporous silicate containing at least one member selected from tungsten, molybdenum and vanadium, which is obtained by:

(i) a step of reacting:

(a) a metal peroxide obtained by reacting at least one metal or metal compound selected from the group consisting of the following 1) to 6) groups with an aqueous hydrogen peroxide solution, 1) tungsten metal, 2) molybdenum metal, 3) vanadium metal, 4) a tungsten compound composed of 4a) tungsten and 4b) at least one element selected from the group consisting of Group 13, Group 14, Group 15 and Group 16 elements except for oxygen, 5) a molybdenum compound composed of 5a) molybdenum and 5b) at least one element selected from the group consisting of Group 13, Group 14, Group 15 and Group 16 elements except for oxygen, and 6) a vanadium compound composed of 6a) vanadium and 6b) at least one element selected from the group consisting of Group 13, Group 14, Group 15 and Group 16 elements except for oxygen, or a solution thereof, with (b) a silicon compound, in the presence of an alkylamine or a quaternary ammonium salt, and (ii) a step of separating the resultant reaction product from the reaction mixture (hereinafter abbreviated as the metallized mesoporous silicate of the present invention); its production process; and further the following production processes which are carried out in the presence of the metallized mesoporous silicate of the present invention:

a process for producing a diol or β-hydroxyhydroperoxide, which comprises reacting hydrogen peroxide and an olefin;

a process for producing a 2-alkoxyalcohol, which comprises reacting hydrogen peroxide, an olefin, and an alcohol;

a process for producing an ester compound, which comprises reacting hydrogen peroxide and a ketone; and a process for producing an aromatic carboxylic acid ester of an alcohol, which comprises reacting hydrogen peroxide, an aromatic aldehyde and the alcohol.

EMBODIMENTS FOR CARRYING OUT THE INVENTION

Figure 1:
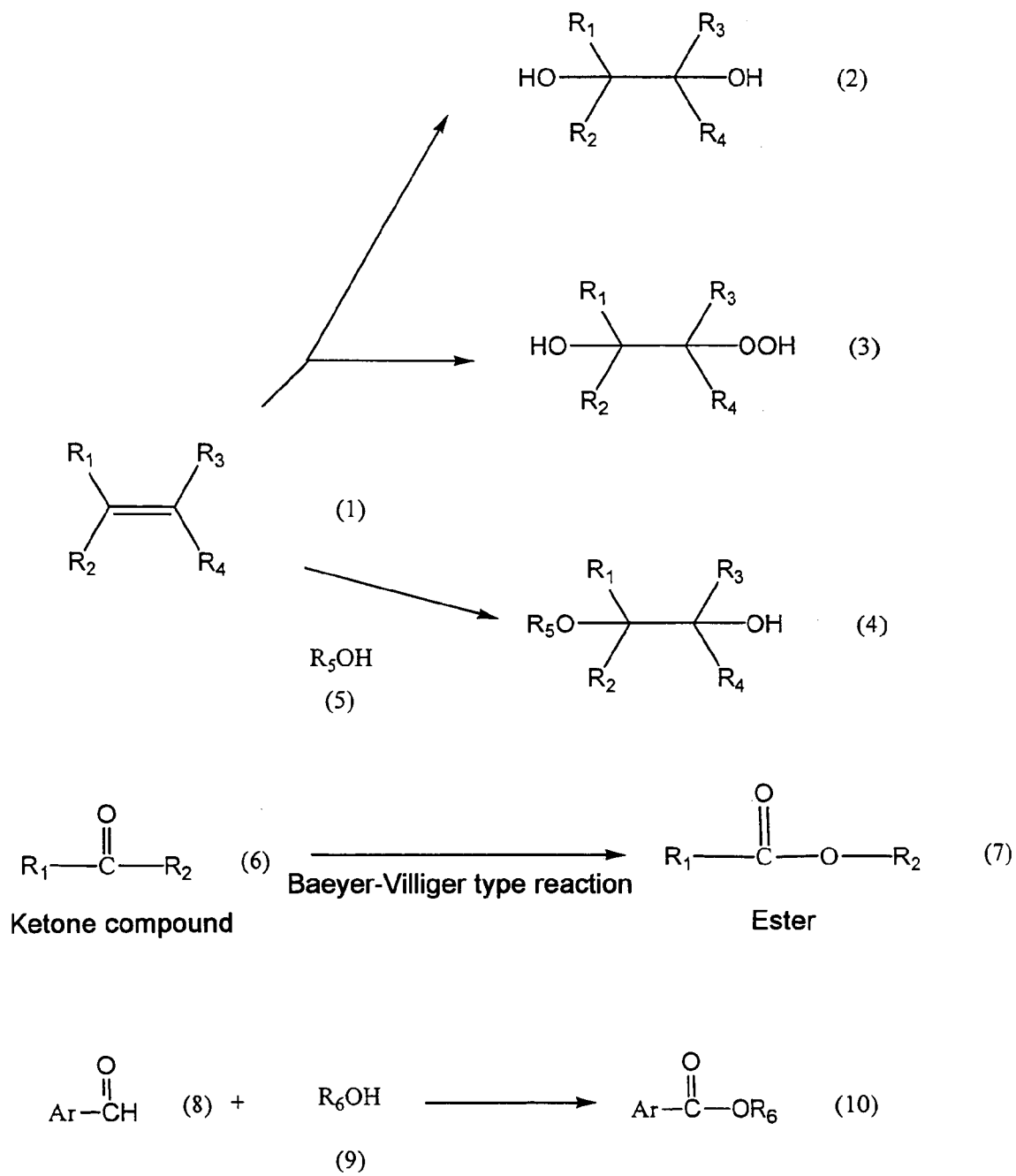
FIG. 1 illustrates an example of a reaction of hydrogen peroxide and an olefin or a carbonyl compound using the metallized mesoporous silicate of the present invention as a catalyst. This exemplifies a process for producing a diol (2) or β-hydroxyhydroperoxide (3) by reacting hydrogen peroxide and an olefin (1), a process for producing a 2-alkoxy alcohol (4) by reacting hydrogen peroxide, an olefin (1), and an alcohol (5), a process for producing an ester compound (7) by reacting hydrogen peroxide and a ketone (6), and a process for producing an aromatic carboxylic acid ester (10) of an alcohol (9) by reacting hydrogen peroxide, an aromatic aldehyde (8) and the alcohol (9).

First, the novel metallized mesoporous silicate containing at least one member selected from the group consisting of tungsten, molybdenum and vanadium of the present invention will be illustrated.

Examples of the tungsten compound include tungsten boride, tungsten carbide, tungsten silicide, tungsten nitride, tungsten phosphide, tungsten sulfide, and the like.

Examples of the molybdenum compound include molybdenum boride, molybdenum carbide, molybdenum silicide, molybdenum nitride, molybdenum phosphide, molybdenum sulfide, and the like.

Examples of the vanadium compound include vanadium boride, vanadium carbide, vanadium silicide, vanadium nitride, vanadium phosphide, vanadium sulfide, and the like.

Further, the metals or metal compounds selected from 1) to 6) groups may be used alone, or two or more of them may be used by mixing. Furthermore, it is preferred to use the metal compound having a smaller particle size because the metal oxide as the catalyst can be easily prepared.

Among them, tungsten metal, molybdenum metal, and vanadium metal are preferably used.

As hydrogen peroxide to be reacted with tungsten metal, molybdenum metal, vanadium metal, the tungsten compound, the molybdenum compound or the vanadium compound (hereinafter, abbreviated as the metal or metal compound), an aqueous solution is usually used. Of course, a solution of hydrogen peroxide in an organic solvent may be used. However, it is preferred to use an aqueous hydrogen peroxide solution from the viewpoint of easy handling. The concentration of hydrogen peroxide in an aqueous hydrogen peroxide solution or in a solution of hydrogen peroxide in an organic solvent is not particularly limited, but in view of volume efficacy and safety, the concentration is practically 1 to 60% by weight. As an aqueous hydrogen peroxide solution, a commercially available aqueous hydrogen peroxide solution is usually used as it is, or if necessary, it may be used by appropriately adjusting the concentration by dilution or concentration. In addition, as a solution of hydrogen peroxide in an organic solvent, a solution prepared by extracting an aqueous hydrogen peroxide solution with an organic solvent, or distilling the solution in the presence of an organic solvent, may be used.

When the oxide of the metal or metal compound is prepared, the amount of hydrogen peroxide to be used is usually 3 moles or more, preferably 5 moles or more relative to 1 mole of the metal or metal compound, and the upper limit of the amount is not particularly defined.

The reaction of the metal or metal compound with hydrogen peroxide is usually carried out in an aqueous solution. Of course, the reaction may be carried out in an organic solvent, for example, an ether solvent such as diethyl ether, methyl tert-butyl ether, tetrahydrofuran, or the like, an ester solvent such as ethyl acetate, and the like, an alcohol solvent such as methanol, ethanol, tert-butanol, and the like, a nitrile solvent such as acetonitrile, propionitrile, and the like, or in a mixture of the organic solvent and water.

The reaction of the metal or metal compound with hydrogen peroxide is usually carried out by mixing and contacting both of them and, in order to improve efficacy of contact between the metal or metal compound, and hydrogen peroxide, preferably, the reaction is carried out with stirring so as to sufficiently disperse the metal or metal compound in a solution for preparing the oxide of the metal or metal compound. The preparation temperature of the oxides of the metal and metal compound is usually −10 to 100° C.

By reacting the metal or metal compound with hydrogen peroxide in water, in an organic solvent, or in a mixed solvent of water and an organic solvent, all or a part of the metal or metal compound is dissolved, whereby, a uniform solution or suspension containing the oxide of the metal or metal compound can be prepared. The oxide of the metal or metal compound may be isolated from the resultant liquid preparation, for example, by concentration, and may be used as a raw material for preparing the metallized mesoporous silicate of the present invention, or the liquid preparation may be used as it is as a raw material.

Examples of the silicon compound include a tetraalkoxysilane such as tetramethoxysilane, tetraethoxysilane, tetraisopropoxysilane, or the like, and the silicon compound is usually used in such an amount that silicon atoms in the tungsten oxide are 4 moles or more relative to 1 mole of the tungsten atom.

Examples of the alkylamine include a primary amine substituted with an alkyl group having 8 to 20 carbon atoms such as octylamine, nonylamine, decylamine, undecylamine, dodecylamine, tridecylamine, tetradecylamine, pentadecylamine, heptadecylamine, octadecylamine, nonadecylamine, eicosylamine, and the like; a secondary methylalkylamine having one methyl group on the substituted primary amine; and the like.

Examples of the quaternary ammonium salt include a hydroxide salt such as tetrapropylammonium hydroxide, tetrabutylammonium hydroxide, trimethyloctylammonium hydroxide, and the like; a quaternary ammonium salt having chlorine or bromine in place of the anion; and the like.

The amount of the alkylamine or quaternary ammonium salt to be used is usually 0.03 to 1 mole relative to 1 mole of the silicon compound.

The reaction of the tungsten oxide with the silicon compound in the presence of the alkylamine or quaternary ammonium salt is usually carried out in the presence of a solvent. Examples of the solvent include water or an alcohol solvent alone or a mixture of the solvents and, preferably, water, and mixtures of water and the alcohol solvent are exemplified. The amount of the solvent to be used is usually 1 to 1000 moles relative to 1 mole of the alkylamine or quaternary ammonium salt.

The reaction temperature is usually 0 to 200° C.

After completion of the reaction, the product obtained is separated, and the separated product is washed or calcined to obtain the metallized mesoporous silicate. For example, a solid produced by the reaction can be separated, if necessary, after crystallization or filtration. Usually, for example, the reaction mixture is filtered, and the resulting filtration residue was washed with water, followed by drying to obtain a solid. If necessary, then, the resulting product is washed with an organic solvent such as methanol, ethanol, and the like to remove the alkylamine or a quaternary ammonium salt, whereby the metallized mesoporous silicate can be obtained. The solid or crystals obtained by separation can be calcined after drying, or, if necessary, they are calcined after washing with water and drying to obtain the desired metallized mesoporous silicate.

Calcination is carried out, for example, at 300 to 700° C. in the atmosphere or under an inert atmosphere.

The metallized mesoporous silicate thus obtained has catalytic capability of an oxidation reaction wherein an organic compound and hydrogen peroxide are reacted to oxidize the organic compound and, at the same time, catalytic capability of an alkylation reaction.

Hereinafter, various oxidation reactions using the metallized mesoporous silicate as a catalyst will be illustrated.

First, the case using an olefin compound will be illustrated. When an olefin compound is used, a diol compound or a β-hydroxyhydroperoxide compound is obtained. By carrying out such a reaction in the presence of an alcohol compound, an O-alkylation reaction proceeds together with an oxidation reaction of the olefin compound. Thus, a 2-alkoxyalcohol compound can also be obtained, as shown in FIG. 1.

The olefin compound is not particularly limited as far as it is an organic compound having an olefinic carbon-carbon double bond. Examples thereof include an unsubstituted olefin in which only hydrogen atoms are bound to the double bond (i.e. ethylene), a mono-substituted olefin compound in which one substituent and three hydrogen atoms are bound to the double bond, a di-substituted olefin compound in which two substituents and two hydrogen atoms are bound to the double bond, a tri-substituted olefin compound in which three substituents and one hydrogen atom are bound to the double bond, and a tetra-substituted olefin compound in which four substituents are bound to the double bond. The substituents ($R_1$ and $R_3$, or $R_2$ and $R_4$ in the compound of the formula (1) in FIG. 1) bound to a carbon-carbon double bond may be taken together to form a part of a ring structure.

Examples of the substituent ($R_1$ to $R_4$ in the compounds of the formulas (1) to (6) in FIG. 1) include a substituted or unsubstituted alkyl group, a substituted or unsubstituted alkoxy group, a substituted or unsubstituted aryl group, a substituted or unsubstituted aryloxy group, a substituted or unsubstituted aralkyl group, a substituted or unsubstituted aralkyloxy group, a halogen atom, a substituted or unsubstituted alkylcarbonyl group, a substituted or unsubstituted arylcarbonyl group, a substituted or unsubstituted aralkylcarbonyl group, a substituted or unsubstituted alkoxycarbonyl group, a substituted or unsubstituted aryloxycarbonyl group, a substituted or unsubstituted aralkyloxycarbonyl group, a carboxyl group, and the like.

Examples of the unsubstituted alkyl group include a straight, branched or cyclic unsubstituted alkyl group having 1 to 20 carbon atoms such as a methyl group, an ethyl group, a n-propyl group, an isopropyl group, a n-butyl group, an isobutyl group, a sec-butyl group, a tert-butyl group, a n-pentyl group, a n-hexyl group, a n-heptyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosyl group, a cyclopentyl group, a cyclohexyl group, a menthyl group, and the like. Examples of the substituted alkyl group include an alkyl group substituted with the following alkoxy group, aryloxy group, aralkyloxy group, halogen atom, alkylcarbonyl group, arylcarbonyl group, aralkylcarbonyl group, alkoxycarbonyl group, aryloxycarbonyl group, aralkyloxycarbonyl group, carboxyl group, or the like. Examples of the specific substituted alkyl group include a chloromethyl group, a fluoromethyl group, a trifluoromethyl group, a methoxymethyl group, an ethoxymethyl group, a methoxyethyl group, a carbomethoxymethyl group, and the like.

Examples of the unsubstituted alkoxy group include an unsubstituted alkoxy group composed of the above unsubstituted alkyl group and an oxygen atom, for example, a straight, branched or cyclic alkoxy group having 1 to 20 carbon atoms such as a methoxy group, an ethoxy group, a n-propoxy group, an isopropoxy group, a n-butoxy group, an isobutoxy group, a sec-butoxy group, a tert-butoxy group, a n-pentyloxy group, a n-hexyloxy group, a n-heptyloxy group, a n-nonyloxy group, a n-decyloxy group, an undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group, a n-eicosyloxy group, a cyclopentyloxy group, a cyclohexyloxy group, a menthyloxy group, or the like. Examples of the substituted alkoxy group include, an alkoxy group having a substituent such as a halogen atom, an alkoxy group, or the like as in the substituted alkyl group above. Examples of the specific substituted alkoxy group include a chloromethoxy group, a fluoromethoxy group, a trifluoromethoxy group, a methoxymethoxy group, an ethoxymethoxy group, a methoxyethoxy group, and the like.

Examples of the unsubstituted aryl group include, for example, a phenyl group, a naphthyl group, and the like. Examples of the substituted aryl group include an aryl group substituted with a substituent such as the above alkyl, aryl, or alkoxy group, as well as with the following aralkyl group such as a benzyl group, aryloxy group, aralkyloxy group, halogen atom, or the like. Examples of the specific substituted aryl group include a 2-methylphenyl group, a 4-chlorophenyl group, a 4-methylphenyl group, a 4-methoxyphenyl group, a 3-phenoxyphenyl group, and the like.

Examples of the substituted or unsubstituted aryloxy group include an aryloxy group composed of the above substituted or unsubstituted aryl group and an oxygen atom. Specific examples thereof include, for example, a phenoxy group, a 2-methylphenoxy group, a 4-chlorophenoxy group, a 4-methylphenoxy group, a 4-methoxyphenoxy group, a 3-phenoxyphenoxy group, and the like.

Examples of the unsubstituted or substituted aralkyl group include an aralkyl group composed of the above unsubstituted or substituted aryl group and the above unsubstituted or substituted alkyl group. Specific examples thereof include, for example, a benzyl group, a 4-chlorobenzyl group, a 4-methylbenzyl group, a 4-methoxybenzyl group, a 3-phenoxybenzyl group, a 2,3,5,6-tetrafluorobenzyl group, a 2,3,5,6-tetrafluoro-4-methylbenzyl group, a 2,3,5,6-tetrafluoro-4-methoxybenzyl group, a 2,3,5,6-tetrafluoro-4-methoxymethylbenzyl group, and the like.

Examples of the substituted or unsubstituted aralkyloxy group include an aralkyloxy group composed of the above substituted or unsubstituted aralkyl group and an oxygen atom. Specific examples thereof include, for example, a benzyloxy group, a 4-chlorobenzyloxy group, a 4-methylbenzyloxy group, a 4-mehoxybenzyloxy group, a 3-phenoxybenzyloxy group, a 2,3,5,6-tetrafluorobenzyloxy group, a 2,3,5,6-tetrafluoro-4-methylbenzyloxy group, a 2,3,5,6-tetrafluoro-4-methoxybenzyloxy group, a 2,3,5,6-tetrafluoro-4-methoxymethylbenzyloxy group, and the like.

Examples of the halogen atom include a fluorine atom, a chlorine atom, a bromine atom, and the like.

Examples of the substituted or unsubstituted alkylcarbonyl group, substituted or unsubstituted arylcarbonyl group, and substituted or unsubstituted aralkylcarbonyl group include groups composed of a carbonyl group and the above substituted or unsubstituted alkyl group, substituted or unsubstituted aryl group or substituted or unsubstituted aralkyl group. Specific examples thereof include, for example, a methylcarbonyl group, an ethylcarbonyl group, a phenylcarbonyl group, a benzylcarbonyl group, and the like.

Examples of the substituted or unsubstituted alkoxycarbonyl group, substituted or unsubstituted aryloxycarbonyl group and substituted or unsubstituted aralkyloxycarbonyl group include groups composed of a carbonyl group and the above substituted or unsubstituted alkoxy group, substituted or unsubstituted aryloxy group, or aralkyloxy group, respectively. Specific examples thereof include, for example, a methoxycarbonyl group, an ethoxycarbonyl group, a phenoxycarbonyl group, a benzyloxycarbonyl group, and the like.

Examples of the olefin compound include 1-hexene, 1-heptene, 1-octene, 1-dodecene, styrene, 4-methylstyrene, 1,7-octadiene, allylbenzene, allylanisole, allyl chloride, allyl ethyl ether, allyl benzyl ether, isobutene, 2-methyl-1-pentene, 2,4,4-trimethyl-1-pentene, 2-ethyl-1-butene, α-methylstyrene, α-phenylstyrene, methylenecyclobutane, methylenecyclopentane, methylenecyclohexane, β-pinene, cyclopentene, cyclohexene, cycloheptene, cyclooctene, 3-methylcyclopentene, 4-methylcyclopentene, 3,4-dimethylcyclopentene, 3,5-dimethylcyclopentene, 3,4,5-trimethylcyclopentene, 3-chlorocyclopentene, 3-methylcyclohexene, 4-methylcyclohexene, 3,4-dimethylcyclohexene, 3,5-dimethylcyclohexene, 3,4,5-trimethylcyclohexene, 2-hexene, 3-hexene, 5-dodecene, norbornene, phenanthrene, 1,2,3,6-tetrahydrophthalic acid anhydride, dicyclopentadiene, indene, methyl 3,3-dimethyl-2-(1-propenyl)cyclopropanecarboxylate, ethyl 3,3-dimethyl-2-(1-propenyl)cyclopropanecarboxylate, 2-methyl-2-pentene, 3-methyl-2-pentene, 3-ethyl-2-pentene, 2-methyl-2-hexene, 3-methyl-2-hexene, 2-methyl-1-phenylpropene, 2-phenyl-2-butene, 1-methylcyclopentene, 1,3-dimethylcyclopentene, 1,4-dimethylcyclopentene, 1,5-dimethylcyclopentene, 1,3,5-trimethylcyclopentene, 1,3,4-trimethylcyclopentene, 1,4,5-trimethylcyclopentene, 1,3,4,5-tetramethylcyclopentene, 1-methylcyclohexene, 1,3-dimethylcyclohexene, 1,4-dimethylcyclohexene, 1,5-dimethylcyclohexene, 1,3,5-trimethylcyclohexene, 1,3,4-trimethylcyclohexene, 1,4,5-trimethylcyclohexene, 1,3,4,5-tetramethylcyclohexene, isophorone, 2-carene, 3-carene, α-pinene, methyl 3,3-dimethyl-2-(2-methyl-1-propenyl)cyclopropanecarboxylate, ethyl 3,3-dimethyl-2-(2-methyl-1-propenyl)cyclopropanecarboxylate, isopropyl 3,3-dimethyl-2-(2-methyl-1-propenyl)cyclopropanecarboxylate, tert-butyl 3,3-dimethyl-2-(2-methyl-1-propenyl)cyclopropanecarboxylate, cyclohexyl 3,3-dimethyl-2-(2-methyl-1-propenyl)cyclopropanecarboxylate, menthyl 3,3-dimethyl-2-(2-methyl-1-propenyl)cyclopropanecarboxylate, benzyl 3,3-diemthyl-2-(2-methyl-1-propenyl)cyclopropanecarboxylate, (4-chlorobenzyl) 3,3-dimethyl-2-(2-methyl-1-propenyl)cyclopropanecarboxylate, (2,3,5,6-tetrafluorobenzyl) 3,3-dimethyl-2-(2-methyl-1-propenyl)cyclopropanecarboxylate, (2,3,5,6-tetrafluoro-4-methylbenzyl) 3,3-dimethyl-2-(2-methyl-1-propenyl)cyclopropanecarboxylate, (2,3,5,6-tetrafluoro-4-methoxybenzyl) 3,3-dimethyl-2-(2-methyl-1-propenyl)cyclopropanecarboxylate, (2,3,5,6-tetrafluoro-4-methoxymethylbenzyl) 3,3-dimethyl-2-(2-methyl-1-propenyl)cyclopropanecarboxylate, (3-phenoxybenzyl) 3,3-diemthyl-2-(2-methyl-1-propenyl) cyclopropanecarboxylate, 2,3-dimethyl-2-butene, 1,2-dimethylcyclopentene, 1,2-dimethylcyclohexene, 1,2,3,4,5,6,7,8-octahydronaphthalene, 1-isopropylidene-2-carboethoxy-3-methylcyclopropane, cyclohexylidenecyclohexane, tetraphenylethylene, 2,3-dimethyl-4-methoxyindene, 2,3-di(4-acetoxyphenyl)-2-butene, and the like.

Among these olefin compounds, there are compounds having asymmetric carbons in the molecules thereof and having optical isomers. In the present invention, optical isomers alone or a mixture thereof may be used.

The amount of the metallized mesoporous silicate catalyst to be used in the reaction of an olefin compound and hydrogen peroxide may be a catalytic amount relative to the olefin compound and is usually 0.001 part by weight or more relative to 1 part by weight of the olefin compound. The upper limit is not particularly defined but, from the economical viewpoint, the amount is practically 1 part by weight or less relative to 1 part by weight of the olefin compound.

Hydrogen peroxide is usually used as an aqueous solution. Of course, a solution of hydrogen peroxide in an organic solvent may be used. The concentration of hydrogen peroxide in an aqueous hydrogen peroxide solution or in a solution in an organic solvent is not particularly limited, but in view of volume efficacy and safety, the concentration is practically 1 to 60% by weight. As an aqueous hydrogen peroxide solution, usually, a commercially available aqueous hydrogen peroxide solution may be used as it is, or if necessary, by adjusting the concentration of hydrogen peroxide thereof by dilution, concentration, and the like. As a solution of hydrogen peroxide in an organic solvent, for example, a solution prepared by means of extraction of an aqueous hydrogen peroxide solution with an organic solvent, distillation of an aqueous hydrogen peroxide solution in the presence of an organic solvent, and the like, may be used.

The amount of hydrogen peroxide to be used for the reaction with an olefin compound is usually 1 mole or more relative to 1 mole of the olefin compound. The upper limit of the amount is not particularly defined, but the amount is practically 10 moles or less relative to 1 mole of the olefin compound from the economical viewpoint.

The reaction of the olefin compound and hydrogen peroxide is usually carried out in water or an organic solvent. Examples of the organic solvent include an ether solvent such as diethyl ether, methyl tert-butyl ether, tetrahydrofuran, or the like, an ester solvent such as ethyl acetate, or the like, a tertiary alcohol solvent such as tert-butanol, or the like, a nitrile solvent such as acetonitrile, propionitrile, or the like, etc. The amount of water or the organic solvent to be used is not particularly limited, but in view of volume efficacy, the amount is practically 100 parts by weight or less relative to 1 part by weight of the olefin compound.

By reacting an olefin compound and hydrogen peroxide in the presence of the metallized mesoporous silicate catalyst of the present invention, a β-hydroxyhydroperoxide compound and a diol compound are obtained. Since a production ratio is different depending on the structure of an olefin compound and reaction conditions, reaction conditions may be appropriately selected according to a particular purpose. In addition, an oxygen-containing organic compound other than a β-hydroxyhydroperoxide compound and a diol compound may be produced as a by-product.

For example, when the reaction is carried out in an organic solvent, the β-hydroxyhydroperoxide compound is apt to be easily obtained as a main product. In addition, since as a water content in a reaction system is smaller, a β-hydroxyhydroperoxide compound is apt to be easily obtained, for selective production of β-hydroxyhydroperoxide compound, it is preferred to carry out the reaction under conditions of a reduced content of water in a reaction system, for example, in the presence of a dehydrating agent in a reaction system. Examples of the dehydrating agent include anhydrous magnesium sulfate, anhydrous sodium sulfate, boric anhydride, polyphosphoric acid, diphosphorus pentaoxide, and the like. The amount to be used may be appropriately determined depending on the amount of water present in the reaction system.

When the reaction temperature is too low, the oxidation reaction hardly proceeds and, when the reaction temperature is too high, a side reaction such as polymerization of a starting olefin compound is liable to proceed. Therefore, the practical reaction temperature is in a range of 0 to 200° C. When the reaction temperature is low, a β-hydroxyhydroperoxide compound is apt to be easily produced and, as the reaction temperature rises higher, a diol compound is apt to be easily produced.

The reaction of an olefin compound and hydrogen peroxide is usually carried out by contacting and mixing the olefin compound, hydrogen peroxide and the metallized mesoporous silicate catalyst, and the order of mixing is not particularly limited. The reaction may be carried out under ordinary pressure conditions, or may be carried out under pressurized conditions. The progress of the reaction can be confirmed by a conventional analytical means such as gas chromatography, high performance liquid chromatography, thin layer chromatography, nuclear magnetic resonance spectrum analysis (hereinafter, abbreviated as NMR), infrared absorption spectrum analysis (hereinafter, abbreviated as IR), and the like.

After completion of the reaction, an oxygen-containing organic compound thus produced can be separated and isolated by subjecting the reaction mixture as it is or, if necessary, after degrading remaining hydrogen peroxide with a reducing agent such as sodium sulfite and filtering off the metallized mesoporous silicate catalyst, to concentration, crystallization, and the like. Further, an oxygen-containing organic compound can be separated and isolated by, if necessary, addition of water and/or a water-insoluble organic solvent to the reaction mixture, followed by extraction and concentration of the resulting organic layer. The oxygen-containing organic compound thus isolated may be further purified by means of distillation, column chromatography, and the like.

Examples of the water-insoluble organic solvent include an aromatic hydrocarbon solvent such as toluene, xylene, and the like, a halogenated hydrocarbon solvent such as dichloromethane, chloroform, chlorobenzene, and the like, an ether solvent such as diethyl ether, methyl tert-butyl ether, tetrahydrofuran, and the like, an ester solvent such as ethyl acetate, and the like, etc. Its amount to be used is not particularly limited.

The metallized mesoporous silicate catalyst or a solution containing the metallized mesoporous silicate catalyst separated from the reaction mixture by filtration, liquid phase separation, and the like can be re-used as a catalyst in the reaction of an olefin compound and hydrogen oxide as it is or, if necessary, after concentration, and the like.

Examples of the β-hydroxyhydroperoxide compound thus obtained (the compound of the formula (3) in FIG. 1) include 1-hydroxy-2-hydroperoxyhexane, 2-hydroxy-1-hydroperoxyhexane, 1-hydroxy-2-hydroperoxyheptane, 2-hydroxy-1-hydroperoxyheptane, 1-hydroxy-2-hydroperoxyoctane, 2-hydroxy-1-hydroperoxyoctane, 1-hydroxy-2-hydroperoxydodecane, 2-hydroxy-1-hydroperoxydodecane, 1-hydroxy-2-phenyl-2-hydroperoxyethane, 1-hydroxy-2-(4-methylphenyl)-2-hydroperoxyethane, 1-hydroxy-2-hydroperoxy-3-phenylpropane, 2-hydroxy-1-hydroperoxy-3-phenylpropane, 1-hydroxy-2-hydroperoxy-3-(4-methoxyphenyl)propane, 2-hydroxy-1-hydroperoxy-3-(4-methoxyphenyl)propane, 1-hydroxy-2-hydroperoxy-3-chloropropane, 2-hydroxy-1-hydroperoxy-3-chloropropane, 1-hydroxy-2-hydroperoxy-3-ethoxypropane, 2-hydroxy-1-hydroperoxy-3-ethoxypropane, (3-hydroxy-2-hydroperoxypropy) benzyl ether, (2-hydroxy-3-hydroperoxyethyl)benzyl ether, methyl 3,3-dimethyl-2-(1-hydroxy-2-hydroperoxyethyl)cyclopropanecarboxylate, methyl 3,3-dimethyl-2-(2-hydroxy-1-hydroperoxyethyl)cyclopropanecarboxylate, ethyl 3,3-dimethyl-2-(1-hydroxy-2-hydroperoxyethyl)cyclopropanecarboxylate, ethyl 3,3-dimethyl-2-(2-hydroxy-1-hydroperoxyethyl)cyclopropanecarboxylate, 2-hydroperoxy-2-methyl-1-propanol, 2,4,4-trimethyl-2-hydroperoxy-1-pentanol, 2-ethyl-2-hydroperoxy-1-butanol, 2-methyl-2-hydroperoxy-1-pentanol, 2-hydroperoxy-2-phenyl-1-propanol, 2,2-diphenyl-2-hydroperoxyethanol, 1-hydroperoxy-1-(hydroxymethyl)cyclobutane, 1-hydroperoxy-1-(hydroxymethyl)

cyclopentane, 1-hydroperoxy-1-(hydroxymethyl) cyclohexane, bicyclo[3.1.1]-2-hydroperoxy-2-(hydroxymethyl)-6,6-dimethylheptane, 1-hydroperoxy-2-hydroxycyclopentane, 1-hydroperoxy-2-hydroxycyclohexane, 1-hydroperoxy-2-hydroxycycloheptane, 1-hydroperoxy-2-hydroxycyclooctane, 1-hydroperoxy-2-hydroxy-3-methylcyclopentane, 1-hydroperoxy-2-hydroxy-4-methylcyclopentane, 1-hydroperoxy-2-hydroxy-3,4-dimethylcyclohexane, 1-hydroperoxy-2-hydroxy-3,4,5-trimethylcyclohexane, 2-hydroperoxy-3-hydroxyhexane, 3-hydroperoxy-2-hydroxyhexane, bicyclo[2.2.1]heptane-2-hydroperoxy-3-ol, methyl 3,3-dimethyl-2-(1-hydroxy-2-hydroperoxypropyl)cyclopropanecarboxylate, methyl 3,3-dimethyl-2-(2-hydroxy-1-hydroperoxypropyl)cyclopropanecarboxylate, ethyl 3,3-dimethyl-2-(1-hydroxy-2-hydroperoxypropyl)cyclopropanecarboxylate, ethyl 3,3-dimethyl-2-(2-hydroxy-1-hydroperoxypropyl)cyclopropanecarboxylate, 2-methyl-2-hydroperoxy-3-hydroxypentane, 3-methyl-3-hydroperoxy-2-hydroxyhexane, 1-methyl-1-hydroperoxy-2-hydroxycyclopentane, 1,3-dimethyl-1-hydroperoxy-2-hydroxycyclohexane, 1,3,5-trimethyl-1-hydroperoxy-2-hydroxycyclohexane, 3-hydroperoxy-4-hydroxycarene, methyl 3,3-dimethyl-2-(2-methyl-2-hydroperoxy-1-hydroxypropyl)cyclopropanecarboxylate, ethyl 3,3-dimethyl-2-(2-methyl-2-hydroperoxy-1-hydroxypropyl)cyclopropanecarboxylate, isopropyl 3,3-dimethyl-2-(2-methyl-2-hydroperoxy-1-hydroxypropyl)cyclopropanecarboxylate, tert-butyl 3,3-dimethyl-2-(2-methyl-2-hydroperoxy-1-hydroxypropyl)cyclopropanecarboxylate, cyclohexyl 3,3-dimethyl-2-(2-methyl-2-hydroperoxy-1-hydroxypropyl)cyclopropanecarboxylate, menthyl 3,3-dimethyl-2-(2-methyl-2-hydroxyperoxy-1-hydroxypropyl)cyclopropanecarboxylate, benzyl 3,3-dimethyl-2-(2-methyl-2-hydroperoxy-1-hydroxypropyl)cyclopropanecarboxylate, (4-chlorobenzyl) 3,3-dimethyl-2-(2-methyl-2-hydroperoxy-1-hydroxypropyl)cyclopropanecarboxylate, (2,3,5,6-tetrafluorobenzyl) 3,3-dimethyl-2-(2-methyl-2-hydroperoxy-1-hydroxypropyl)cyclopropanecarboxylate, (2,3,5,6-tetrafluoro-4-methylbenzyl) 3,3-dimethyl-2-(2-methyl-2-hydroperoxy-1-hydroxypropyl)cyclopropanecarboxylate, (2,3,5,6-tetrafluoro-4-methoxybenzyl) 3,3-dimethyl-2-(2-methyl-2-hydroperoxy-1-hydroxypropyl)cyclopropanecarboxylate, (2,3,5,6-tetrafluoro-4-methoxymethylbenzyl) 3,3-dimethyl-2-(2-methyl-2-hydroperoxy-1-hydroxypropyl)cyclopropanecarboxylate, (3-phenoxybenzyl) 3,3-dimethyl-2-(2-methyl-2-hydroperoxy-1-hydroxypropyl)cyclopropanecarboxylate, 2,3-dimethyl-2-hydroperoxy-3-hydroxybutane, 1,2-dimethyl-1-hydroperoxy-2-hydroxycyclopentane, 1,2-dimethyl-1-hydroperoxy-2-hydroxycyclohexane, bicyclo[4.4.0]-1-hydroperoxy-6-hydroxydecane, 1-hydroxyperoxy-1-(1-hydroxy-1-methylethyl)-2,3-dimethylcyclopentane, 1-hydroxy-1-(1-hydroperoxy-1-methylethyl)-2,3-dimethylcyclopentane, 1-hydroperoxy-1-(1-hydroxycyclohexyl)cyclohexane, 1-hydroperoxy-1-hydroxy-1,1,2,2-tetraphenylethane, 2-hydroperoxy-3-hydroxy-2,3-dimethyl-4-methoxyindane, 2-hydroxy-3-hydroperoxy-2,3-dimethyl-4-methoxyindane, 2,3-di(4-acetoxyphenyl)-2-hydroperoxy-3-hydroxybutane, and the like.

Examples of the diol compound (the compound of the formula (2) in FIG. 1) include 1,2-hexanediol, 1,2-haptanediol, 1,2-octanediol, 1,2-dodecanediol, phenylethylene glycol, (4-methylphenyl)ethylene glycol, 3-phenyl-1,2-propanediol, 3-(4-methoxyphenyl)-1,2-propanediol, 3-chloro-1,2-propanediol, 3-ethoxy-1,2-propanediol, 3-benzyloxy-1,2-propanediol, methyl 3,3-dimethyl-2-(1,2-dihydroxyethyl) cyclopropanecarboxylate, 1,2-cyclopentanediol, 1,2-cyclohexanediol, 1,2-cycloheptanediol, 1,2-cyclooctanediol, 3-methyl-1,2-cyclopentanediol, 4-methyl-1,2-cyclopentanediol, 3,4-dimethyl-1,2-cyclohexanediol, 3,4,5-trimethyl-1,2-cyclohexanediol, 2,3-hexanediol, bicyclo[2.2.1]heptane-2,3-diol, methyl 3,3-dimethyl-2-(1,2-dihydroxypropyl)cyclopropanecarboxylate, ethyl 3,3-dimethyl-2-(1,2-dihydroxypropyl)cyclopropanecarboxylate, 2-methyl-1,2-propanediol, 2-methyl-1,2-pentanediol, 2,4,4-trimethyl-1,2-pentanediol, 2-ethyl-1,2-butanediol, 2-phenyl-1,2-propanediol, 1,1-diphenyl-1,2-ethanediol, 1-(hydroxymethyl)cyclobutanol, 1-(hydroxymethyl)cyclopentanol, 1-(hydroxymethyl)cyclohexanol, bicyclo[4.1.1]-2-hydroxymethyl-6,6-dimethylheptane-2-ol, 2-methyl-2,3-pentanediol, 3-methyl-2,3-hexanediol, 1-methyl-1,2-cyclopentanediol, 1-methyl-1,2-cyclohexanediol, 1,3-dimethyl-1,2-cyclohexanediol, 1,3,5-trimethyl-1,2-cyclohexanediol, 3,4-carenediol, methyl 3,3-dimethyl-2-(2-methyl-1,2-dihydroxypropyl)cyclopropanecarboxylate, ethyl 3,3-dimethyl-2-(2-methyl-1,2-dihydroxypropyl)cyclopropanecarboxylate, isopropyl 3,3-dimethyl-2-(2-methyl-1,2-dihydroxypropyl)cyclopropanecarboxylate, tert-butyl 3,3-dimethyl-2-(2-methyl-1,2-dihydroxypropyl)cyclopropanecarboxylate, cyclohexyl 3,3-dimethyl-2-(2-methyl-1,2-dihydroxypropyl)cyclopropanecarboxylate, menthyl 3,3-dimethyl-2-(2-methyl-1,2-dihydroxypropyl)cyclopropanecarboxylate, benzyl 3,3-dimethyl-2-(2-methyl-1,2-dihydroxypropyl)cyclopropanecarboxylate, (4-chlorobenzyl) 3,3-dimethyl-2-(2-methyl-1,2-dihydroxypropyl)cyclopropanecarboxylate, (2,3,5,6-tetrafluorobenzyl) 3,3-dimethyl-2-(2-methyl-1,2-dihydroxypropyl)cyclopropanecarboxylate, (2,3,5,6-tetrafluoro-4-methylbenzyl) 3,3-dimethyl-2-(2-methyl-1,2-dihydroxypropyl)cyclopropanecarboxylate, (2,3,5,6-tetrafluoro-4-methoxybenzyl) 3,3-dimethyl-2-(2-methyl-1,2-dihydroxypropyl)cyclopropanecarboxylate, (2,3,5,6-tetrafluoro-4-methoxymethylbenzyl) 3,3-dimethyl-2-(2-methyl-1,2-dihydroxypropyl)cyclopropanecarboxylate, (3-phenoxybenzyl) 3,3-dimethyl-2-(2-methyl-1,2-dihydroxypropyl)cyclopropanecarboxylate, pinacol, 1,2-dimethyl-1,2-cyclopentanediol, 1,2-dimethyl-1,2-cyclohexanediol, 1,2-di(4-acetoxyphenyl)-1,2-butanediol, bicyclo[4.4.0]decane-1,6-diol, 1,1,2,2-tetraphenylethylene glycol, 2,3-dihydroxy-2,3-dimethyl-4-methoxyindane, and the like.

When an optically active substance is used as an olefin compound, an optically active oxygen-containing organic compound is obtained according to a position of an asymmetric carbon.

By carrying out the above reaction of the olefin compound and hydrogen peroxide in the presence of a primary alcohol compound or a secondary alcohol compound (hereinafter, abbreviated as an alcohol compound), an O-alkylation reaction proceeds together with the oxidation reaction of the olefin compound, whereby, a 2-alkoxyalcohol compound is obtained.

Examples of the alcohol compound (the compound represented by the formula (5): $R_5OH$ in FIG. 1) include a primary alcohol compound or a secondary alcohol compound having 1 to 4 carbon atoms such as methanol, ethanol, n-propanol, isopropanol, n-butanol, isobutanol, and the like.

The amount of the alcohol compound to be used is usually 1 mole or more relative to 1 mole of the olefin compound to be used, and an upper limit is not particularly defined. For example, the alcohol compound may be used in large excess relative to the olefin compound so as to also serve as a reaction solvent.

The reaction temperature is usually 0 to 200° C. and, as a reaction temperature rises higher, a 2-alkoxyalcohol compound is apt to be easily produced.

Examples of the 2-alkoxyalcohol compound (the compound represented by the formula (4) in FIG. 1) include 1-hydroxy-2-methoxyhexane, 2-hydroxy-1-methoxyhexane, 1-hydroxy-2-ethoxyheptane, 2-hydroxy-1-ethoxyheptane, 1-hydroxy-2-propoxyoctane, 2-hydroxy-1-propoxyoctane, 1-hydroxy-2-methoxydodecane, 2-hydroxy-1-methoxydodecane, 1-hydroxy-2-phenyl-2-ethoxyethane, 1-hydroxy-2-(4-methylphenyl)-2-ethoxyethane, 1-hydroxy-2-methoxy-3-phenylpropane, 2-hydroxy-1-methoxy-3-phenylpropane, 1-hydroxy-2-ethoxy-3-(4-methoxyphenyl)propane, 2-hydroxy-1-ethoxy-3-(4-methoxyphenyl)propane, 1-hydroxy-2-propoxy-3-chloropropane, 2-hydroxy-1-propoxy-3-chloropropane, 1-hydroxy-2-methoxy-3-ethoxypropane, 2-hydroxy-l-methoxy-3-ethoxypropane, (3-hydroxy-2-ethoxypropyl) benzyl ether, (2-hydroxy-3-ethoxyethyl) benzyl ether, 2-methoxy-2-methyl-1-propanol, 2,4,4-trimethyl-2-methoxy-1-pentanol, 2-ethyl-2-ethoxy-1-butanol, 2-methyl-2-propoxy-1-pentanol, 2-methoxy-2-phenyl-1-propanol, 2,2-diphenyl-2-butoxyethanol, 1-methoxy-1-(hydroxymethyl)cyclobutane, 1-ethoxy-1-(hydroxymethyl)cyclopentane, 1-methoxy-1-(hydroxymethyl)cyclohexane, bicyclo[3.1.1]-2-ethoxy-2-(hydroxymethyl)-6,6-dimethylheptane, 1-methoxy-2-hydroxycyclopentane, 1-ethoxy-2-hydroxycyclohexane, 1-propoxy-2-hydroxycycloheptane, 1-butoxy-2-hydroxycyclooctane, 1-methoxy-2-hydroxy-3-methylcyclopentane, 1-ethoxy-2-hydroxy-4-methylcyclopentane, 1-propoxy-2-hydroxy-3,4-dimethylcyclohexane, 1-butoxy-2-hydroxy-3,4,5-trimethylcyclohexane, 2-methoxy-3-hydroxyhexane, 3-ethoxy-2-hydroxyhexane, bicyclo[2.2.1]heptane-2-propoxy-3-ol, methyl 3,3-dimethyl-2-(1-hydroxy-2-ethoxypropyl)cyclopropanecarboxylate, methyl 3,3-dimethyl-2-(2-hydroxy-1-methoxypropyl)cyclopropanecarboxylate, ethyl 3,3-diemthyl-2-(1-hydroxy-2-methoxypropyl)cyclopropanecarboxylate, ethyl 3,3-dimethyl-2-(2-hydroxy-1-butoxypropyl)cyclopropanecarboxylate, 2-methyl-2-methoxy-3-hydroxypentane, 3-methyl-3-ethoxy-2-hydroxyhexane, 1-methyl-1-propoxy-2-hydroxycyclopentane, 1,3-dimethyl-1-butoxy-2-hydroxycyclohexane, 1,3,5-trimethyl-1-methoxy-2-hydroxycyclohexane, 3-ethoxy-4-hydroxycarene, methyl 3,3-dimethyl-2-(2-methyl-2-methoxy-1-hydroxypropyl)cyclopropanecarboxylate, ethyl 3,3-dimethyl-2-(2-methyl-2-ethoxy-2-hydroxypropyl)cyclopropanecarboxylate, isopropyl 3,3-dimethyl-2-(2-methyl-2-propoxy-1-hydroxypropyl)cyclopropanecarboxylate, tert-butyl 3,3-dimethyl-2-(2-methyl-2-butoxy-1-hydroxypropyl)cyclopropanecarboxylate, cyclohexyl 3,3-dimethyl-2-(2-methyl-2-methoxy-1-hydroxypropyl)cyclopropanecarboxylate, menthyl 3,3-dimethyl-2-(2-methyl-2-methoxy-1-hydroxypropyl)cyclopropanecarboxylate, benzyl 3,3-dimethyl-2-(2-methyl-2-ethoxy-1-hydroxypropyl)cyclopropanecarboxylate, (4-chlorobenzyl) 3,3-diemthyl-2-(2-methyl-2-ethoxy-1-hydroxypropyl)cyclopropanecarboxylate, (2,3,5,6-tetrafluorobenzyl) 3,3-dimethyl-2-(2-methyl-2-propoxyl-1-hydroxypropyl)cyclopropanecarboxylate, (2,3,5,6-tetrafluoro-4-methylbenzyl) 3,3-dimethyl-2-(2-methyl-2-propoxy-1-hydroxypropyl)cyclopropanecarboxylate, (2,3,5,6-tetrafluoro-4-methoxybenzyl) 3,3-dimethyl-2-(2-methyl-2-butoxy-1-hydroxypropyl)cyclopropanecarboxylate, (2,3,5,6-tetrafluoro-4-methoxymethylbenzyl) 3,3-dimethyl-2-(2-methyl-2-butoxy-1-hydroxypropyl)cyclopropanecarboxylate, (3-phenoxybenzyl) 3,3-dimethyl-2-(2-methyl-2-methoxy-1-hydroxypropyl)cyclopropanecarboxylate, 2,3-dimethyl-2-methoxy-3-hydroxybutane, 1,2-dimethyl-1-hydroperoxy-2-ethoxycyclopentane, 1,2-dimethyl-1-ethoxy-2-hydroxycyclohexane, bicyclo[4.4.0]-1-propoxy-6-hydroxydecane, 1-propoxy-1-(1-hydroxy-1-methylethyl)-2,3-dimethylcyclopentane, 1-hydroxy-1-(1-methoxy-1-methylethyl)-2,3-dimethylcyclopentane, 1-methoxy-1-(1-hydroxycyclohexyl)cyclohexane, 1-ethoxy-1-hydroxy-1,1,2,2-tetraphenylethane, 2-propoxy-3-hydroxy-2,3-dimethyl-4-methoxyindane, 2-hydroxy-3-butoxy-2,3-dimethyl-4-methoxyindane, 2,3-di(4-acetoxyphenyl)-2-methoxy-3-hydroxybutane, and the like.

Then, a reaction using a ketone compound will be illustrated. When a ketone compound is used, a Baeyer-Villiger reaction product is obtained. As shown in FIG. 1, for example, when a cyclic ketone compound is used as the ketone compound, a lactone compound is obtained.

Examples of the ring structure of the cyclic ketone compound include a cyclobutane ring, a cyclopentane ring, a cyclohexane ring, a cycloheptane ring, a cyclooctane ring, a cyclononane ring, a cyclodecane ring, a cyclododecane ring, a benzene ring, and the like, and such a ring may be substituted with an alkyl group, an alkoxy group, an aryl group, a halogen atom, or the like.

Examples of the substituent represented by $R_1$ or $R_2$ include the groups as described above. Examples of the alkyl group include a straight, branched or cyclic alkyl group such as a methyl group, an ethyl group, a n-propyl group, an isopropyl group, a n-butyl group, an isobutyl group, a sec-butyl group, a tert-butyl group, a n-pentyl group, a n-hexyl group, a n-octyl group, an isooctyl group, a n-nonyl group, a n-decyl group, a cyclopentyl group, a cyclohexyl group, and the like. The alkyl group may have a substituent, and examples of the substituent include an alkoxy group such as a methoxy group, an ethoxy group, a n-propxy group, an isopropoxy group, a n-butoxy group, and the like, and a halogen atom such as a fluorine atom, a chlorine atom, a bromine atom, and the like. Examples of the alkyl group having the substituent include a chloromethyl group, a fluoromethyl group, a trifluoromethyl group, a methoxymethyl group, a methoxyethyl group, and the like.

Examples of the aryl group include a phenyl group, a naphthyl group, and the like, and the aryl group may have a substituent. Examples of the substituent include the above alkyl group, the above alkoxy group, the above halogen atom, and an acyl group such as an acetyl group, a propionyl group, and the like, etc. and examples of the aryl group substituted with the substituent include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 2-methylphenyl group, a 4-methylphenyl group, a 4-methoxyphenyl group, a 4-acetylphenyl group, and the like.

Examples of the cyclic ketone compound include cyclopropanone, cyclobutanone, 3-methylcyclobutanone, 3-phenylcyclobutanone, cyclopentanone, 2-methylcyclopentanone, 2-phenylcyclopentanone, cyclohexanone, 2-methylcyclohexanone, 2-phenylcyclohexanone, 4-methylcyclohexanone, 4-phenylcyclohexanone, 4-chlorocyclohexaone, cycloheptanone, cyclooctanone, cyclodecanone, cyclododecanone, 1,4-cyclohexanedione, adamantanone, and the like.

The amount of the metallized mesoporous silicate catalyst to be used in the reaction of the ketone compound and hydrogen peroxide may be a catalytic amount relative to the ketone compound, and is usually 0.001 part by weight or more relative to 1 part by weight of the ketone compound. The upper limit is not particularly defined but, from the economical viewpoint, the amount is practically 1 part by weight or less relative to 1 part by weight of the ketone compound.

As hydrogen peroxide, an aqueous solution is usually used. Of course, a solution of hydrogen peroxide in an organic solvent may be used. The concentration of hydrogen peroxide in an aqueous hydrogen peroxide solution or in a solution of hydrogen peroxide in an organic solvent is not particularly limited, but in view of volume efficacy and safety, the concentration is practically 1 to 60% by weight. As an aqueous hydrogen peroxide solution, usually, a commercially available aqueous hydrogen peroxide solution may be used as it is, or if necessary, by adjusting the concentration thereof by dilution, concentration, and the like. As a solution of hydrogen peroxide in an organic solvent, for example, a solution prepared by means of extraction of an aqueous hydrogen peroxide solution with an organic solvent, distillation of an aqueous hydrogen peroxide solution in the presence of an organic solvent, and the like, may be used.

The amount of hydrogen peroxide to be used is usually 0.4 mole or more, preferably 1 mole or more relative to 1 mole of the ketone compound. The upper limit is not particularly defined but, when the amount is too large, it is liable to be economically disadvantageous. Then, the amount is practically 10 mole or less relative to 1 mole of a ketone compound.

The reaction of the ketone compound and hydrogen peroxide may be carried out without a solvent, or may be carried out in water, in an organic solvent, or in a mixture of water and an organic solvent. Examples of the organic solvent include an ether solvent such as diethyl ether, methyl tert-butyl ether, diglyme, or the like, a tertiary alcohol solvent such as tert-butanol, or the like, a nitrile solvent such as acetonitrile, propionitrile, or the like, etc.

The reaction of the ketone compound and hydrogen peroxide is usually carried out by contacting and mixing the metallized mesoporous silicate catalyst, the ketone compound and hydrogen peroxide, and the order of mixing is not particularly limited.

The reaction temperature is usually −10 to 130° C., and the reaction is usually carried out at ordinary pressure, or may be carried out under reduced pressure or pressurized conditions.

As the reaction proceeds, a lactone compound is produced, and the progress of the reaction can be confirmed by a conventional analytical means such as gas chromatography, high performance liquid chromatography, thin layer chromatography, NMR, IR, and the like.

After completion of the reaction, the desired lactone compound can be isolated by subjecting the reaction mixture as it is, or, if necessary, after degrading remaining hydrogen peroxide with a reducing agent such as sodium sulfite, and separating the metallized mesoporous silicate by filtration, and the like, to concentration, crystallization and the like. Further, by addition of water and/or a water-insoluble organic solvent to the reaction mixture, if necessary, followed by extraction and concentration of the resulting organic layer, a lactone compound can be isolated. The isolated lactone compound may be further purified by a conventional purification method such as distillation, column chromatography, recrystallization, and the like.

The metallized mesoporous silicate catalyst or a solution of the metallized mesoporous silicate catalyst separated by filtration, liquid phase separation, and the like can be re-used as a catalyst in the reaction of a ketone compound and hydrogen oxide as it is, or, if necessary, after concentration, and the like.

Examples of the thus obtained lactone compound include β-propiolactone, γ-butyrolactone, β-methyl-γ-butyrolactone, β-phenyl-γ-butyrolactone, δ-valerolactone, ε-valerolactone, α-phenyl-δ-valerolactone, δ-phenyl-δ-valerolactone, ε-caprolactone, α-methyl-ε-caprolactone, ε-methyl-ε-caprolactone, α-phenyl-ε-caprolactone, ε-phenyl-ε-caprolactone, and the like.

Then, a process for producing an aromatic carboxylic acid ester of an alcohol by reacting an aromatic aldehyde compound and the alcohol compound will be illustrated.

The aromatic ring (which is represented by Ar in FIG. 1) of the aromatic aldehyde compound may be substituted with the same alkyl group, alkoxy group, aryl group, and halogen atom as those defined with respect to the above $R_1$ to $R_4$, and the like.

Examples of the alkyl group include straight, branched or cyclic alkyl groups such as a methyl group, an ethyl group, a n-propyl group, an isopropyl group, a n-butyl group, an isobutyl group, a sec-butyl group, a tert-butyl group, a n-pentyl group, a n-hexyl group, a n-octyl group, an isooctyl group, a n-nonyl group, a n-decyl group, a cyclopentyl group, a cyclohexyl group, and the like. The alkyl group may have a substituent, and examples of the substituent include an alkoxy group such as a methoxy group, an ethoxy group, a n-propoxy group, an isopropoxy group, a n-butoxy group, or the like, and a halogen atom such as a fluorine atom, a chlorine atom, a bromine atom, or the like. Examples of the alkyl group having the substituent include a chloromethyl group, a fluoromethyl group, a trifluoromethyl group, a methoxymethyl group, a methoxyethyl group, and the like.

Examples of the aryl group include a phenyl group, a naphthyl group, and the like, and the aryl group may have a substituent. Examples of the substituent include the above alkyl group, the above alkoxy group, the above halogen atom, an acyl group such as an acetyl group, a propionyl group, or the like, etc. Examples of the aryl group substituted with the substituent include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 2-methylphenyl group, a 4-methylphenyl group, a 4-methoxyphenyl group, a 4-acetylphenyl group, and the like.

Examples of the aromatic aldehyde compound include benzaldehyde, 2-fluorobenzaldehyde, 2-chlorobenzaldehyde, 2-bromobenzaldehyde, 3-fluorobenzaldehyde, 3-chlorobenzaldehyde, 3-bromobenzaldehyde, 4-fluorobenzaldehyde, 4-chlorobenzaldehyde, 4-bromobenzaldehyde, 2,4-difluorobenzaldehyde, 2,4-dichlorobenzaldehyde, 3,5-difluorobenzaldehyde, 3-phenoxybenzaldehyde, 4-methylbenzaldehyde, 3-trifluoromethylbenzaldehyde, 2-methoxybenzaldehyde, 1-naphthylaldehyde, and the like.

Examples of the alcohol compound include the alcohol compound represented by the formula (9): $R_6OH$ [wherein $R_6$ represents a $C_{1-4}$ primary or secondary alkyl group] in FIG. 1, and specific examples include a primary alcohol compound and a secondary alcohol compound having 1 to 4 carbon atoms such as methanol, ethanol, n-propanol, isopropanol, n-butanol, isobutanol, and the like.

The amount of the alcohol compound to be used is usually 1 mole or more relative to 1 mole of the olefin compound to be used, and its upper limit is not particularly defined. For example, the alcohol compound may be used in large excess relative to the olefin compound so as to also serve as a reaction solvent.

The amount of the metallized mesoporous silicate catalyst to be used in the reaction of the aromatic aldehyde compound and hydrogen peroxide which is carried out in the presence of the alcohol compound may be a catalytic amount, and is usually 0.001 part by weight or more relative to 1 part by weight of the aromatic aldehyde compound. Its upper limit is not particularly defined, but from the economical viewpoint, the amount is practically 1 part by weight or less relative to 1 part by weight of the aromatic aldehyde compound.

As hydrogen peroxide, an aqueous solution is usually used. Of course, a solution of hydrogen peroxide in an organic solvent may be used. The concentration of hydrogen peroxide in an aqueous hydrogen peroxide solution or in a solution of hydrogen peroxide in an organic solvent is not particularly limited, but in view of volume efficacy and safety, the concentration is practically 1 to 60% by weight. As an aqueous hydrogen peroxide solution, usually, a commercially available aqueous hydrogen peroxide solution may be used as it is, or, if necessary, by adjusting the concentration thereof by dilution, concentration, and the like. As a solution of hydrogen peroxide in an organic solvent, for example, a solution prepared by extracting an aqueous hydrogen peroxide solution with an organic solvent, or distilling an aqueous hydrogen peroxide solution in the presence of an organic solvent, may be used.

The amount of hydrogen peroxide to be used is usually 0.4 mole or more, preferably 1 mole or more relative to 1 mole of the aromatic aldehyde compound. Its upper limit is not particularly defined, but when the amount rises too much, it is liable to be economically disadvantageous. Then, the amount is practically 10 moles or less.

The reaction of the aromatic aldehyde compound and hydrogen peroxide which is carried out in the presence of the alcohol compound may be carried out by using the alcohol compound as a solvent, as described above, or may be carried out in water, in an organic solvent, or in a mixture of water and an organic solvent. Examples of the organic solvent include an ether solvent such as diethyl ether, methyl tert-butyl ether, diglyme, or the like, a nitrile solvent such as acetonitrile, propionitrile, or the like, etc.

The reaction of the aromatic aldehyde compound and hydrogen peroxide which is carried out in the presence of the alcohol compound is usually carried out by contacting and mixing the metallized mesoporous silicate catalyst, the aromatic aldehyde compound, the alcohol compound and hydrogen peroxide, and the order of mixing is not particularly limited.

The reaction temperature is usually −10 to 130° C., and the reaction is usually carried out at ordinary pressure, but may be carried out under reduced pressure or pressurized conditions.

As the reaction proceeds, the aromatic ester compound is produced, and the progress of the reaction can be confirmed by a conventional analytical means such as gas chromatography, high performance liquid chromatography, thin layer chromatography, NMR, IR, and the like.

After completion of the reaction, the desired aromatic ester compound can be isolated by subjecting the reaction mixture as it is, or if necessary, after degrading remaining hydrogen peroxide with a reducing agent such as sodium sulfite, and separating the metallized mesoporous silicate catalyst by filtration, or the like, to concentration, crystallization, and the like. Alternatively, the aromatic ester compound can be isolated by, extracting the reaction mixture, if necessary, by adding water and/or a water-insoluble organic solvent thereto, and concentrating the resulting organic layer. The isolated aromatic ester compound may be further purified by a conventional purification method such as distillation, column chromatography, recrystallization, and the like.

The metallized mesoporous silicate catalyst, or a solution containing the metallized mesoporous silicate catalyst separated by filtration, liquid phase separation, and the like, may be re-used as a catalyst for the reaction of the aromatic aldehyde compound and hydrogen peroxide which is carried out in the presence of the alcohol compound, as it is, or if necessary, after concentration, and the like.

Examples of the aromatic ester compound thus obtained include methyl benzoate, ethyl 2-fluorobenzoate, propyl 2-chlorobenzoate, butyl 2-bromobenzoate, methyl 3-fluorobenzoate, ethyl 3-chlorobenzoate, methyl 3-bromobenzoate, ethyl 4-fluorobenzoate, methyl 4-chlorobenzoate, methyl 4-bromobenzoate, methyl 2,4-difluorobenzoate, methyl 2,4-dichlorobenzoate, methyl 3,5-difluorobenzoate, methyl 3-phenoxybenzoate, methyl 4-benzoate, methyl 3-trifluoromethylbenzoate, methyl 2-methoxybenzoate, 1-carbomethoxynaphthalene, and the like.

EXAMPLES

The following Examples further illustrate the present invention in detail, but the present invention is not limited by these Examples. The analysis was carried out by gas chromatography (hereinafter, abbreviated as GC) and high performance liquid chromatography (hereinafter, referred to as LC). Respective analytical conditions are as follows:

<GC Analytical Conditions>

Column: DB-1 ($\phi$0.25 µm×30 m, membrane thickness 1.0 µm)

Carrier gas: helium (flow rate: 1 m/min)

Split ratio: 1/10, Sample injection amount: 1 µL

Column temperature: 100° C. (0 min)→180° C. (temperature raising rate: 2° C./min, retention time at 180° C.: 0 min)→300° C. (temperature raising rate: 10° C./min, retention time at 300° C.: 15 min)

Injection inlet temperature: 200° C., detector temperature: 250° C.

<LC Analytical Conditions>

Column: SUMIPAX ODS A-212 (5 µm, $\phi$6 mm×15 cm)

Mobile phase: A solution, 0.1% by volume aqueous trifluoroacetic acid solution

B solution, 0.1% by volume trifluoroacetic acid/acetonitrile solution

The composition was linearly changed from A solution/B solution=90/10 (volume ratio) to A solution/B solution=10/90 (volume ratio) for 40 minutes, and was retained at the composition ratio of A solution/B solution=10/90 (volume ratio) for 20 minutes.

Flow rate: 1.0 mL/min, sample injection amount: 10 µL, detection wavelength: 220 nm

Example 1

<Preparation of Tungsten-Containing Mesoporous Silicate using Alkylamine>

To a 500 mL flask equipped with an induction stirrer were added 1 g of a tungsten metal powder and 5 g of ion-exchanged water, an inner temperature was raised to 40° C., 3 g of a 60% by weight aqueous hydrogen peroxide solution was added dropwise thereto over 30 minutes, and the mixture was maintained at the same temperature for 1 hour to obtain a tungsten oxide-containing solution. To the tungsten oxide-containing solution were added 100 g of ion-exchanged water and 80 g of ethanol, and then 10 g of dodecylamine was added dropwise thereto at an inner temperature of 40° C. over 30 minutes. Then, the mixture was cooled to an inner temperature of 25° C., and 41.6 g of tetraethoxysilane was added dropwise thereto over 30 minutes. When stirring was continued at an inner temperature of 25° C., crystals precipitated in about 30 minutes to form slurry, and this was further stirred and maintained at the same temperature for 24 hours. From the resulting slurry, crystals were collected by filtration, washed with 100 g of ion-exchanged water twice, and dried at 110° C. for 6 hours. The white crystals were calcined at 550° C. for 6 hours to obtain 15.0 g of a white solid.

XRD spectrum: A broad peak having an apex at a d value of 3.79 Å is observed. A peak assignable to tungsten oxide is not observed.

IR spectrum of the resulting solid (KBr) $v_{max}$: 3471, 1636, 1080, 972, 804 cm$^{-1}$ Elemental analysis value: W, 2.43%; Si, 35.6%

Specific surface area (nitrogen absorption method): 696 m$^2$/g

Micropore diameter (nitrogen absorption method): 32 Å

Example 2

<Preparation of Tungsten-Containing Mesoporous Silicate using Quaternary Ammonium Salt>

To a 500 mL flask equipped with an induction stirrer were added 5 g of a tungsten metal powder and 25 g of ion-exchanged water, an inner temperature was raised to 40° C., 15 g of a 60% by weight aqueous hydrogen peroxide solution was added dropwise thereto over 30 minutes, and the mixture was maintained at the same temperature for 1 hour to obtain a tungsten oxide-containing solution. To the tungsten oxide-containing solution were added 75 g of ion-exchanged water and 80 g of ethanol, and then 8 g of tetrabutylammonium hydroxide salt was added dropwise thereto at an inner temperature of 40° C. over 30 minutes. Then, the mixture was cooled to an inner temperature of 25° C., and 41.6 g of tetraethoxysilane was added dropwise thereto over 30 minutes. When stirring was continued at an inner temperature of 25° C., crystals were precipitated in about 30 minutes to form slurry, and this was stirred and maintained at the same temperature for 24 hours. From the resulting slurry, crystals were collected by filtration, washed with 100 g of ion-exchanged water twice, and dried at 130° C. for 24 hours to obtain 33.0 g of white crystals. 16.0 g of the white crystals were calcined at 550° C. for 6 hours to obtain 7.8 g of a white solid.

XRD spectrum: A spectrum of a mixture of a broad peak having an apex at a d value of 3.79 Å, and a sharp peak assignable to tungsten oxide is observed.

IR spectrum of the resulting solid (KBr) $v_{max}$: 3484, 1642, 1081, 950, 813, 783 cm$^{-1}$ Elemental analysis value: W, 23.9%; Si, 28.4%

Specific surface area (nitrogen absorption method): 514 m$^2$/g

Micropore diameter (nitrogen absorption method): 32 Å

Example 3

<Preparation of Tungsten-Containing Mesoporous Silicate using Quaternary Ammonium Salt>

To a 500 mL flask equipped with an induction stirrer were added 5 g of a tungsten metal powder and 25 g of ion-exchanged water, an inner temperature was raised to 40° C., 15 g of a 60% by weight aqueous hydrogen peroxide solution was added dropwise over 30 minutes thereto, and the mixture was maintained at the same temperature for 2 hours to obtain a tungsten oxide-containing solution. To the tungsten oxide-containing solution were added 75 g of ion-exchanged water and 80 g of ethanol, 41.6 g of tetraethoxysilane was charged therein at an inner temperature of 40° C. over 10 minutes, and 20 g of a 40% aqueous tetrabutylammonium hydroxide solution was added dropwise thereto over 10 minutes. Then, the mixture was cooled to an inner temperature of 25° C. and, when stirring was continued, crystals were precipitated in about 30 minutes to form slurry, and the mixture was stirred and maintained at the same temperature for 24 hours. From the resulting slurry, crystals were collected by filtration, washed with 100 g of ion-exchanged water twice, and dried at 130° C. for 24 hours to obtain 38.0 g of white crystals. The white crystals were calcined at 550° C. for 6 hours to obtain 16.5 g of a white solid.

XRD spectrum: A broad peak having an apex at a d value of 3.77 Å is observed. A sharp peak assignable to tungsten oxide is not observed.

IR spectrum of the resulting solid (KBr) $v_{max}$: 3478, 1638, 1078, 960, 806, 557 cm$^{-1}$ Elemental analysis value: W, 9.8%; Si, 39.5%

Specific surface area (nitrogen absorption method): 543 m$^2$/g

Micropore diameter (nitrogen absorption method): 16 Å

Example 4

<Preparation of Tungsten-Containing Mesoporous Silicate using Quaternary Ammonium Salt>

To a 500 mL flask equipped with an induction stirrer were added 5 g of a tungsten metal powder and 25 g of ion-exchanged water, an inner temperature was raised to 40° C., 15 g of a 60% by weight aqueous hydrogen peroxide solution was added dropwise thereto over 30 minutes, and the mixture was maintained at the same temperature for 2 hours to obtain a tungsten oxide-containing solution. To the tungsten oxide-containing solution were added 75 g of ion-exchanged water and 80 g of ethanol, 41.6 g of tetraethoxysilane was charged therein at an inner temperature of 40° C. over 10 minutes, and 40 g of a 10% tetrapropylammonium hydroxide solution was added dropwise thereto over 10 minutes. Then, the mixture was cooled to an inner temperature of 25° C. and, when stirring was continued, crystals were precipitated in about 30 minutes to form slurry, and the mixture was stirred and maintained at the same temperature for 24 hours. From the resulting slurry solution, crystals were collected by filtration, washed with 100 g of ion-exchanged water twice, and dried at 130° C. for 24 hours to obtain 38.0 g of white crystals. The white crystals were calcined at 550° C. for 6 hours to obtain 17.3 g of a white solid.

XRD spectrum: A broad peak having an apex at a d value of 3.76 Å is observed. A sharp peak assignable to tungsten oxide is slightly observed.

IR spectrum of the resulting solid (KBr) $\phi_{max}$: 3480, 1638, 1078, 956, 800 cm$^{-1}$ Elemental analysis value: W, 11.0%; Si, 31.4%

Specific surface area (nitrogen absorption method): 573 m$^2$/g

Micropore diameter (nitrogen absorption method): 22 Å

Comparative Example 1

<Preparation of Tungsten-Containing Mesoporous Silicate using Quaternary Ammonium Salt>

According to the same manner as that of Example 4, 15.0 g of a white solid was obtained except that 6.8 g of tungstic acid was used in place of 5 g of the tungsten metal powder in Example 4.

XRD spectrum: A broad peak having an apex at a d value of 3.89 Å is observed. A sharp peak assignable to tungsten oxide is slightly observed.

IR spectrum of the resulting solid (KBr) $\upsilon_{max}$: 3480, 1638, 1080, 952, 794 cm$^{-1}$ Elemental analysis value: W, 19.6%; Si, 30.9%

Specific surface area (nitrogen absorption method): 267 m$^2$/g

Micropore diameter (nitrogen absorption method): 23 Å

Example 5

<Preparation of Molybdenum-Containing Mesoporous Silicate using Alkylamine>

To a 500 mL flask equipped with an induction stirrer were added 2 g of a molybdenum metal powder and 25 g of ion-exchanged water, an inner temperature was raised to 40° C., 15 g of a 60% by weight aqueous hydrogen peroxide solution was added dropwise thereto over 1 hour, and the mixture was maintained at the same temperature for 1 hour to obtain a molybdenum oxide-containing solution. To the molybdenum oxide-containing solution were added 75 g of ion-exchanged water and 80 g of ethanol, 41.6 g of tetraethoxysilane was added thereto at an inner temperature of 40° C. over 10 minutes, and then 10 g of dodecyl amine was added dropwise over thereto 10 minutes. Crystals were precipitated immediately to form slurry and, then, the mixture was cooled to an inner temperature of 25° C., and stirred and maintained at the same temperature for 24 hours. From the resulting slurry, crystals were collected by filtration, washed with 100 g of ion-exchanged water twice, and dried at 110° C. for 6 hours. The white crystals were calcined at 550° C. for 6 hours to obtain 15.5 g of a white solid.

XRD spectrum: A mixed spectrum of a broad peak having an apex at a d value of 3.8 Å and a sharp peak assignable to molybdenum oxide is observed.

IR spectrum of resulting solid (KBr) $\upsilon_{max}$: 3470, 1640, 1090, 956, 915, 802 cm$^{-1}$ Elemental analysis value: Mo, 13.9%; Si, 32.4%

Specific surface area (nitrogen absorption method): 171 m$^2$/g

Micropore diameter (nitrogen absorption method): 73 Å

Example 6

<Preparation of Molybdenum Containing Mesoporous Silicate using Quaternary Ammonium Salt>

To a 500 mL flask equipped with an induction stirrer were added 2.5 g of a molybdenum metal powder and 25 g of ion-exchanged water, an inner temperature was raised to 40° C., 15 g of a 60% by weight aqueous hydrogen peroxide solution was added dropwise thereto over 1 hour, and the mixture was maintained at the same temperature for 1 hour to obtain a molybdenum oxide-containing solution. To the molybdenum oxide-containing solution were added 75 g of ion-exchanged water and 80 g of ethanol, 41.6 g of tetraethoxysilane was added thereto at an inner temperature of 40° C. over 10 minutes, and then 20 g of a 40% aqueous tetrabutylammonium hydroxide solution was added dropwise thereto over 10 minutes. Crystals were precipitated in about 15 minutes to form slurry, 200 g of ion-exchanged water was further added thereto, and the mixture was cooled to an inner temperature of 25° C., and stirred and maintained at the same temperature for 24 hours. From the resulting slurry, crystals were collected by filtration, washed with 100 g of ion-exchanged water twice, and dried at 110° C. for 6 hours. The white crystals were calcined at 550° C. for 6 hours to obtain 15.9 g of a white solid.

XRD spectrum: A broad peak having an apex at a d value of 3.79 Å is observed. A sharp peak assignable to molybdenum oxide is not observed.

IR spectrum of the resulting solid (KBr) $\upsilon_{max}$: 3470, 1640, 1080, 956, 913, 796 cm$^{-1}$ Elemental analysis value: Mo, 5.22%; Si, 37.0%

Specific surface area (nitrogen absorption method): 649 m$^2$/g

Micropore diameter (nitrogen absorption method): 22 Å

Example 7

<Preparation of Vanadium-Containing Mesoporous Silicate using Quaternary Ammonium Salt>

To a 500 mL flask equipped with an induction stirrer were added 1.3 g of a vanadium metal powder and 25 g of ion-exchanged water, an inner temperature was raised to 40° C., 15 g of a 30% by weight aqueous hydrogen peroxide solution was added dropwise thereto over 30 minutes, and the mixture was maintained at the same temperature for 1 hour to obtain a vanadium oxide-containing solution. To the vanadium oxide-containing solution were added 75 g of ion-exchanged water and 80 g of ethanol, 41.6 g of tetraethoxysilane was added thereto at an inner temperature of 40° C. for 10 minutes, and then 40 g of a 40% aqueous tetra-n-propylamine solution was added dropwise thereto over 10 minutes. Then, the mixture was cooled to an inner temperature of 25° C., when stirring was continued, crystals were precipitated in about 30 minutes to form slurry, and the mixture was stirred and maintained at the same temperature for 24 hours. From the resulting slurry, crystals were collected by filtration, washed with 100 g of ion-exchanged water twice, and dried at 130° C. for 8 hours. The white crystals were calcined at 550° C. for 6 hours to obtain 16.0 g of a brown solid.

XRD spectrum: A broad peak having an apex at a d value of 3.85 Å is observed.

IR spectrum of resulting solid (KBr) $\upsilon_{max}$: 1050, 956, 794, 629 cm$^{-1}$ Elemental analysis value: V, 5.56%; Si, 36.1%

Example 8

To a 50 mL flask equipped with a magnetic stirrer and a reflux condenser were added 800 mg of the tungsten-containing mesoporous silicate prepared in Example 1, 800 mg of a 60% by weight aqueous hydrogen peroxide solution, 2 g of tert-butanol and 400 mg of 1-heptene, and the mixture was stirred and maintained at an inner temperature of 40° C. for 16 hours to react these materials. To the resulting reaction mixture was added 5 g of methyl tert-butyl ether, and the mixture was stirred, and then allowed to stand. The supernatant organic layer was analyzed by LC, and it was found that 2-hydroperoxy-1-hydroxyheptane and 1-hydroperoxy-2-hydroxyheptane were produced. When the organic layer was analyzed by GC, 2-hydroperoxy-1-hydroxyheptane and 1-hydroperoxy-2-hydroxyheptane were thermally decomposed at an injection inlet, and detected as 1-hexanal. Then, the yield of 1-hexanal was determined by GC analysis (internal standard method), and this was regarded as the yield of 2-hydroperoxy-1-hydroxyheptane and 1-hydroperoxy-2-hydroxyheptane. Yield: 22%. The recovery of 1-hexene was 67%.

Example 9

To a 50 mL flask equipped with a magnetic stirrer and a refluxing condensing tube were added 300 mg of the tungsten-containing mesoporous silicate prepared in Example 2, 760 mg of 60% by weight aqueous hydrogen peroxide solution, 3 g of tert-butanol and 500 mg of 1-octene, and the mixture was stirred and maintained at an inner temperature of 50° C. for 16 hours to react these materials. To the resulting reaction mixture was added 5 g of methyl tert-butyl ether, and the mixture was stirred, and allowed to stand. The supernatant organic layer was analyzed by LC, and it was found that 2-hydroperoxy-1-hydroxyoctane and 1-hydroperoxy-2-hydroxyoctane were produced. When the organic layer was analyzed by GC, 2-hydroperoxy-1-hydroxyoctane and 1-hydroperoxy-2-hydroxyoctane were thermally decomposed at an injection inlet, and detected as 1-heptanal. Then, the yield of 1-heptanal was determined by GC analysis (internal standard method), and this was regarded as the yield of 2-hydroperoxy-1-hydroxyoctane and 1-hydroperoxy-2-hydroxyoctane. Yield: 42%

Example 10

To a 50 mL flask equipped with a magnetic stirrer and a refluxing condensing tube were added 200 mg of the tungsten-containing mesoporous silicate synthesized in Example 1, 285 mg of 60% by weight aqueous hydrogen peroxide solution, 24 g of ethanol and 410 mg of cyclohexene, and the mixture was stirred and maintained at an inner temperature of 80° C. for 6 hours to react these materials. The resulting reaction mixture was analyzed by GC (internal standard method), and the yield of the products was determined.

Yield of 2-ethoxycyclohexanol: 50%
Yield of 1,2-cyclohexanediol: 5%
The recovery of the starting material, cyclohexene, was 40%.

Example 11

To 50 mL flask equipped with a magnetic stirrer and a refluxing condensing tube were added 200 mg of the tungsten-containing mesoporous silicate synthesized in Example 3, 285 mg of a 60% by weight aqueous hydrogen peroxide solution, 24 g of ethanol and 410 mg of cyclohexene, and the mixture was stirred and maintained at an inner temperature of 80° C. for 6 hours to react these materials. The resulting reaction mixture was analyzed by GC (internal standard method), and the yield of the products was determined.

Yield of 2-ethoxycyclohexanol: 61%
Yield of 1,2-cyclohexanediol: 1.7%

The recovery of the starting material, cyclohexene, was 35%.

Example 12

To a 100 mL flask equipped with a magnetic stirrer and a reflux condenser were added 300 mg of the tungsten-containing mesoporous silicate synthesized in Example 2, 10 g of methanol and 3.08 g of cyclohexene, and an inner temperature was raised to 65° C. A mixed solution containing 4.3 g of a 30% by weight aqueous hydrogen peroxide solution and 10 g of methanol was added dropwise thereto with stirring over 3 hours, and the mixture was maintained for 1 hour. The resulting reaction solution was analyzed by GC (internal standard method), and the yield of the products was determined.

Yield of 2-methoxycyclohexanol: 33%
1,2-Cyclohexanediol was not detected.
The recovery of the starting material, cyclohexene, was 65%.

Example 13

According to a similar manner as that of Example 12, the yield of the products was determined except that 300 mg of the tungsten-containing mesoporous silicate synthesized in Example 3 was used in place of the tungsten-containing mesoporous silicate synthesized in Example 2, in Example 12.

Yield of 2-methoxycyclohexanol: 42.1%
1,2-Cyclohexanediol was not detected.
The recovery of the starting material, cyclohexene, was 55%.

Example 14

According to a similar manner as that of Example 12, the yield of the products was determined except that 300 mg of the tungsten-containing mesoporous silicate synthesized in Example 4 was used in place of the tungsten-containing mesoporous silicate synthesized in Example 2, in Example 12.

Yield of 2-methoxycyclohexanol: 64%
Yield of 1,2-cyclohexanediol: 1%
The recovery of the starting material, cyclohexene, was 33%.

Comparative Example 2

According a similar manner as that of Example 12, the yield of the products was determined except that 300 mg of the tungsten-containing mesoporous silicate synthesized in Comparative Example 1 was used in place of the tungsten-containing mesoporous silicate synthesized in Example 2, in Example 12.

Yield of 2-methoxycyclohexanol: 35%
Yield of 1,2-cyclohexanediol: 8%
The recovery of the starting material, cyclohexene, was 53%.

Example 15

According to a similar manner as that of Example 12, the yield of the products was determined except that 300 mg of the molybdenum-containing mesoporous silicate synthesized in Example 5 was used in place of the tungsten-containing mesoporous silicate synthesized in Example 2, in Example 12.

Yield of 2-methoxycyclohexanol: 55.4%
Yield of 1,2-cyclohexanediol: 1%
The recovery of the starting material, cyclohexene, was 42%.

Example 16

According to a similar manner as that of Example 12, the yield of the products was determined except that 300 mg of the molybdenum-containing mesoporous silicate synthesized in Example 6 was used in place of the tungsten-containing mesoporous silicate synthesized in Example 2, in Example 12.

Yield of 2-methoxycyclohexanol: 28.5%
1,2-Cyclohexanediol was not detected.
The recovery of the starting material, cyclohexene, was 70%.

Example 17

A 100 mL flask equipped with a magnetic stirrer and a refluxing condensing tube was charged with 50 mg of the tungsten-containing mesoporous silicate synthesized in Example 2, 5 g of methanol and 500 mg of benzaldehyde, and an inner temperature was raised to 65° C. A mixed solution containing 1.6 g of a 30% by weight aqueous hydrogen peroxide solution and 5 g of methanol was added dropwise with stirring thereto over 3 hours, and the mixture was maintained for 1 hour. The resulting reaction mixture was analyzed by GC (internal standard method), and the yield of the products was determined.

Yield of benzoic acid methyl ester: 71%
The recovery of the starting material, benzaldehyde, was 25%.

Example 18

According to a similar manner as that of Example 17, the yield of the products was determined except that 50 mg of the tungsten-containing mesoporous silicate synthesized in Example 4 was used in place of the tungsten-containing mesoporous silicate synthesized in Example 2, in Example 17.

Yield of benzoic acid methyl ester: 75%
The recovery of the starting material, benzaldehyde, was 20%.

Example 19

According to a similar manner as that of Example 17, the yield of the products was determined except that 50 mg of the molybdenum-containing mesoporous silicate synthesized in Example 5 was used in place of the tungsten-containing mesoporous silicate synthesized in Example 2, in Example 17.

Yield of benzoic acid methyl ester: 75%
The recovery of the starting material, benzaldehyde, was 20%.

Example 20

According to a similar manner as that of Example 17, the yield of the products was determined except that 50 mg of the vanadium-containing mesoporous silicate synthesized in Example 7 was used in place of the tungsten-containing mesoporous silicate synthesized in Example 2, in Example 17.

Yield of benzoic acid methyl ester: 95%
The recovery of the starting material, benzaldehyde, was 2%.

Example 21

To a 50 mL flask equipped with a magnetic stirrer and a refluxing condensing tube were added 100 mg of the tungsten-containing mesoporous silicate synthesized in Example 2, 340 mg of a 60% by weight aqueous hydrogen peroxide solution, 5 g of acetonitrile and 500 mg of cyclopentanone, and the mixture was stirred and maintained at an inner temperature of 80° C. for 4 hours to react these materials. The resulting reaction mixture was analyzed by GC (internal standard method), the yield of the products was determined.

Yield of δ-valerolactone: 22.1%.
The recovery of the starting material, cyclopentanone, was 77%.

INDUSTRIAL APPLICABILITY

According to the present invention, metallized mesoporous silicate obtained by reacting a silicon compound, and metal peroxide obtained by reacting any one selected from easily available tungsten metal, molybdenum metal, vanadium metal, and the aforementioned metal compound thereof, with hydrogen peroxide, in the presence of alkylamine or quaternary ammonium salt, has oxidation reaction catalytic activity and, at the same time, alkylation reaction catalytic activity, and is an advantageous catalyst from an industrially point of view. For example, by reacting hydrogen peroxide which is an inexpensive oxidizing agent, with an organic compound such as an olefin compound and a ketone compound in the presence of the metallized mesoporous silicate catalyst of the present invention, oxygen-containing organic compounds such as a β-hydroxyhydroperoxide compound, a diol compound, a lactone compound, a 2-alkoxyalcohol compound, and an aromatic ester compound can be produced.

The invention claimed is:

1. A metallized mesoporous silicate containing at least one member selected from tungsten, molybdenum and vanadium, which is obtained by:
   (i) a step of reacting:
      (a) a metal peroxide obtained by reacting at least one metal or metal compound selected from the group consisting of the following 1) to 3) groups with aqueous hydrogen peroxide solution,
         1) tungsten metal, 2) molybdenum metal, 3) vanadium metal, or a solution thereof, with
      (b) a silicon compound, in the presence of an alkylamine or a quaternary ammonium salt, and
   (ii) a step of separating the resultant reaction product from the reaction mixture.

2. The metallized mesoporous silicate according to claim 1, wherein the silicon compound is a tetraalkoxysilane.

3. The metallized mesoporous silicate according to claim 1, wherein the alkylamine is a primary amine.

4. The metallized mesoporous silicate according to claim 1, wherein the quaternary ammonium salt is a tetraalkylammonium hydroxide.

5. A process for producing a diol or β-hydroxyhydroperoxide, which comprises reacting hydrogen peroxide and an olefin in the presence of the metallized mesoporous silicate according to claim 1.

6. A process for producing a 2-alkoxyalcohol, which comprises reacting hydrogen peroxide, an olefin, and an alcohol in the presence of the metallized mesoporous silicate according to claim 1.

7. A process for producing an ester compound, which comprises reacting hydrogen peroxide and a ketone in the presence of the metallized mesoporous silicate according to claim 1.

8. The process according to claim 7, wherein the ketone is a cyclic ketone, and a Baeyer-Villiger reaction product is a cyclic lactone.

9. A process for producing an aromatic carboxylic acid ester of an alcohol, which comprises reacting hydrogen peroxide, an aromatic aldehyde and the alcohol in the presence of the metallized mesoporous silicate according to claim 1.

10. A process for producing a metallized mesoporous silicate containing at least one member selected from tungsten, molybdenum and vanadium, which comprises:
(i) a step of reacting:
(a) a metal peroxide obtained by reacting at least one metal or metal compound selected from the group consisting of the following 1) to 6) groups with an aqueous hydrogen peroxide solution,
1) tungsten metal, 2) molybdenum metal, 3) vanadium metal,
4) a tungsten compound composed of 4a) tungsten and 4b) at least one element selected from the group consisting of Group 13, Group 14, Group 15 and Group 16 elements except for oxygen,
5) a molybdenum compound composed of 5a) molybdenum and 5b) at least one element selected from the group consisting of Group 13, Group 14, Group 15 and Group 16 elements except for oxygen, and
6) a vanadium compound composed of 6a) vanadium and 6b) at least one element selected from the group consisting of Group 13, Group 14, Group 15 and Group 16 elements except for oxygen, or a salt thereof, with
(b) a silicon compound, in the presence of an alkylamine or a quaternary ammonium salt, and
(ii) a step of separating the resultant reaction product from the reaction mixture.

11. The process for producing metallized mesoporous silicate according to claim 10, wherein the silicon compound is a tetraalkoxysilane.

12. The process for producing metallized mesoporous silicate according to claim 10, wherein the alkylamine is a primary amine.

13. The process for producing metallized mesoporous silicate according to claim 10, wherein the quaternary ammonium salt is a tetraalkylammonium hydroxide.

* * * * *